United States Patent [19]
Hidaka

[11] Patent Number: 5,466,066
[45] Date of Patent: Nov. 14, 1995

[54] THERMOGRAVIMETRIC APPARATUS WITH A BALANCE ARM VIBRATING FUNCTION

[75] Inventor: Akihiko Hidaka, Tokyo, Japan

[73] Assignee: Seiko Instruments Inc., Tokyo, Japan

[21] Appl. No.: 184,027

[22] Filed: Jan. 21, 1994

[30] Foreign Application Priority Data

Jan. 21, 1993 [JP] Japan ................... 5-008504

[51] Int. Cl.$^6$ .............. G01N 25/00; G01N 5/00
[52] U.S. Cl. ........................................... 374/14
[58] Field of Search ................. 374/14; 177/245

[56] References Cited

U.S. PATENT DOCUMENTS

| | | | |
|---|---|---|---|
| 3,045,472 | 7/1962 | Paulik et al. | 374/14 |
| 4,606,649 | 8/1986 | Mikhail | 374/14 |
| 4,846,292 | 7/1989 | Narukawa | 374/14 |
| 5,306,087 | 4/1994 | Nakamura et al. | 374/14 |

FOREIGN PATENT DOCUMENTS

| | | | |
|---|---|---|---|
| 0053556 | 3/1986 | Japan | 374/14 |
| 404256830 | 9/1992 | Japan | 374/14 |

*Primary Examiner*—Diego F. F. Gutierrez
*Attorney, Agent, or Firm*—Spensley Horn Jubas & Lubiz

[57] ABSTRACT

In a thermogravimetric apparatus which is composed of a balance-arm 1, a detector 2 for detecting an amount of deviation of the balance-arm 1, a control circuit 3 for controlling equilibrium of the balance, and a driving part 6 for moving the balance-arm to the balanced position, vibration of the balance-arm has been made possible by adding a vibration generating circuit 5 for vibrating the balance-arm 1 and an adding circuit 4 for adding a signal from the control circuit 3 to a signal from the vibration generating circuit 5. A measurement which is excellent in reproducibility and accuracy is thus obtained. Automation of replacement of samples and unattended measurement are also made possible.

2 Claims, 1 Drawing Sheet

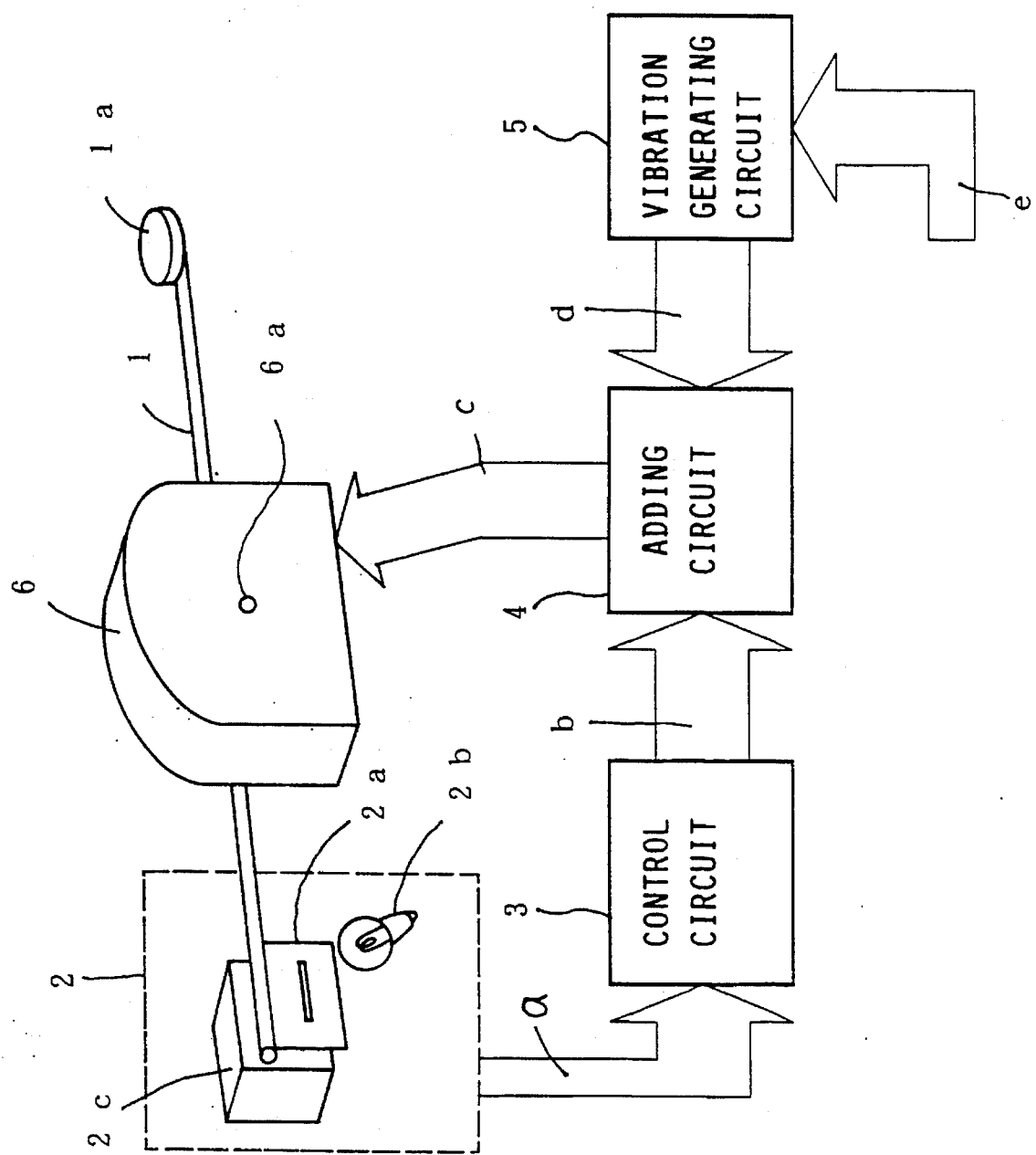

THERMOGRAVIMETRIC APPARATUS WITH A BALANCE ARM VIBRATING FUNCTION

BACKGROUND OF THE INVENTION

The invention relates to a thermal analysis apparatus and particularly to a thermogravimetric apparatus.

An existing thermogravimetric apparatus according to the prior art holds a sample on a dish-shaped sample holder set at the end of a balance-arm and heats the sample by means of a heating furnace according to a specified heating program, and measures weight change of the sample by means of the balance-arm.

And a sample is set on a sample holder usually by hand. Such an existing apparatus does not set an sample in a correct position by itself in case that the sample is put in an incorrect position deviated from the correct position on the sample holder.

The above-mentioned prior art has a disadvantage that it is necessary to move a sample by hand since it is impossible to obtain good reproducibility and accuracy of measurement in case that measurement is made in a state where the sample is placed in an incorrect position on the sample holder.

So, an object of the invention is to make it possible to move the sample to a correct position on the sample holder automatically instead of manually.

SUMMARY OF THE INVENTION

The invention has been made to remove the above-mentioned disadvantage, and a means of the invention is mainly composed of a balance-arm having a sample holder, a detector for detecting an amount of deviation of the balance-arm from the balanced position, a control circuit for controlling equilibrium of the balance-arm, a vibration generating circuit for vibrating the balance-arm, an arithmetic device for performing an arithmetic operation between a signal from the control circuit and a signal from the vibration generating circuit, and a driving part for moving the balance-arm to the balanced position.

The means composed as described above performs a balance-arm controlling action of an existing thermogravimetric apparatus, first, when the vibration generating circuit is outputting a level of zero without outputting a vibrational wave. Namely, when the balance-arm comes to be in an unbalanced state, an amount of deviation from the balanced position is outputted as a displacement signal by the detector. The displacement signal is inputted into the control circuit and turned into a control signal for moving the balance-arm to the balanced position and the control signal is entered into the arithmetic device. Since output of the vibration generating circuit is at a level of zero according to the above-mentioned conditions, the arithmetic circuit outputs the control signal as a driving signal of the balance-arm as it is. The driving part receives the control signal and moves the balance-arm to the balanced position. A series of actions described above are ordinary balance-arm controlling actions. On the other hand, when the vibration generating circuit is outputting a vibrational wave, the balance-arm is vibrated since the vibrational wave is added to or subtracted from the control signal in a series of balance-arm controlling actions described above. Vibrating the balance-arm makes it possible to move a sample to the correct position on the sample holder without manual intervention even in case that the sample is placed in an incorrect position on the sample holder and attains the object of the invention.

Namely, since the sample holder has the shape of a part of a concave spherical surface, a sample placed out of a specified position on the sample holder is automatically moved to the lowest point (the specified position) of the sample holder by vibrating the balance-arm and is set in the correct position.

BRIEF DESCRIPTION OF DRAWING

The FIG. 1 is a block diagram showing an embodiment of the invention.

DESCRIPTION OF THE PREFERRED EMBODIMENTS

Referring to the drawings showing an embodiment of the invention, the invention is described in detail in the following.

In the FIG. 1, a balance-arm 1 which has a sample holder 1a at one end of it and a detector 2 for detecting displacement of the balance-arm 1 at the other end of it is supported by a shaft 6a of a driving part 6 so as to be freely turned around the shaft 6a.

The sample holder 1 has the shape of a part of a concave spherical surface and is lowest in its central position. The detector 2 is composed of a slit plate 2a having a slit passing a light through it which is set at the other end of the balance-arm 1, a light source 2b for passing a light through the slit, and a light detector 2c for detecting the light which has passed through the slit. Deviation of the balance-arm 1 can be detected by detecting the light which has passed through the slit by means of the light detector 2c. Namely, change in weight of the sample can be detected.

A method of measuring weight change (weight itself) of a sample in general is described in the following.

Ordinary balance-arm controlling actions are made in which the balance-arm 1 is not vibrated. Namely, output of a vibration generating circuit 5 is set at a level of zero by means of a control signal "e". In the above-mentioned state, in case that the balance-arm 1 is deviated out of the balanced position, the amount of the deviation is converted into an electric signal of a displacement signal "a". The displacement signal a is inputted into a control circuit 3 and outputted as a control signal "b" to restore the balance-arm to the balanced position. An adding circuit 4 adds the control signal "b" and a vibrational wave "d" to each other, but since the vibrational wave "d" is kept at a level of zero in the ordinary balance-arm controlling action, the control signal "b" is outputted to a driving part 6 as a driving signal "c" as it is. The driving part 6 receives the driving signal "c" and moves the balance-arm to the balanced position. The driving signal "c" at this time becomes a parameter of weight change (weight itself) of the sample and the thermogravimetric measurement is ended. A series of actions described above are balance-arm controlling actions in a thermogravimetric apparatus.

Next, though description is in wrong order, a case of placing a sample on the sample holder 1a at the beginning of measurement is described.

After putting a sample on the sample holder 1a, the driving part 6 is controlled by the driving signal "c" so as to make level the balance-arm 1 as described above. Next, the balance-arm is vibrated so that the sample may come to a specified position on the sample holder 1a. At this time, the vibration generating circuit 5 outputs the vibrational wave "d" according to the control signal "e". At this time, adding the vibrational wave "d" to the control signal "b" in a series of actions described above by means of the adding circuit 4 makes a driving signal "c" and the driving part 6 vibrates the balance-arm 1. By vibrating the balance-arm 1 in this manner, it is possible to move a sample to the correct position without manual intervention even in case that the sample is placed in an incorrect position on the sample holder. And by causing the vibrational wave "d" to the balance-arm to have a continuously changing frequency, this method can be applied to samples of various weights.

As described above, the invention makes it possible to make measurements having excellent reproducibility and accuracy by making it possible to move a sample to a correct position without manual intervention by means of a function of vibrating a balance even in case that the sample is placed in an incorrect position on the sample holder. And the invention has also an effect of making possible an automatic replacement or an unattended measurement of samples as a result of making replacement by hand unnecessary.

What is claimed is:

1. A thermogravimetric apparatus comprising;

a balance-arm having a sample holder, a detector for detecting an amount of deviation of the balance-arm from a balanced position, a control circuit for producing a control signal for controlling equilibrium of the balance-arm, a driving part for moving the balance-arm to the balanced position, a vibration generating circuit for generating a vibration signal having a frequency, and an arithmetic device connected for receiving the control signal and the vibration signal and for performing an arithmetic operation on the control signal and the vibration signal to produce a driving signal which is supplied to said driving part for vibrating said balance-arm.

2. A thermogravimetric apparatus as defined in claim 1, wherein the frequency of the vibration signal generated by said vibration generating circuit is continuously changed.

* * * * *